(12) United States Patent
Bamba et al.

(10) Patent No.: US 8,394,368 B2
(45) Date of Patent: *Mar. 12, 2013

(54) METHOD FOR PRODUCING A COMPOSITION FOR PROMOTING SURVIVAL OF TRANSPLANTED HEMATOPOIETIC STEM CELL

(75) Inventors: Kenzo Bamba, Ibaraki (JP); Yasuyuki Kuroiwa, Ibaraki (JP); Tomohiro Morio, Tokyo (JP); Norio Shimizu, Yamanashi (JP)

(73) Assignee: Lymphotec Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/987,780

(22) Filed: Jan. 10, 2011

(65) Prior Publication Data

US 2011/0097314 A1   Apr. 28, 2011

Related U.S. Application Data

(62) Division of application No. 12/556,162, filed on Sep. 9, 2009, now abandoned, which is a division of application No. 10/559,448, filed as application No. PCT/JP2004/007164 on May 26, 2004, now abandoned.

(30) Foreign Application Priority Data

Jun. 3, 2003 (JP) ................................. 2003-157996
May 7, 2004 (JP) ................................. 2004-138468

(51) Int. Cl.
*C12N 5/08* (2006.01)
*C12N 5/00* (2006.01)
*A61K 38/21* (2006.01)
*C07K 1/00* (2006.01)
*A01N 63/00* (2006.01)

(52) U.S. Cl. .................... 424/85.4; 424/93.71; 435/372; 435/386; 530/351

(58) Field of Classification Search .................. None
See application file for complete search history.

(56) References Cited

U.S. PATENT DOCUMENTS

| 4,994,481 A | 2/1991 | Zimmer et al. |
| 6,352,694 B1 | 3/2002 | June et al. |
| 6,692,958 B2 | 2/2004 | Sekine et al. |
| 6,905,874 B2 | 6/2005 | Berenson et al. |
| 7,435,592 B2 | 10/2008 | Har-Noy |

FOREIGN PATENT DOCUMENTS

| JP | 03080076 | 4/1991 |
| WO | 9705239 A1 | 2/1997 |

OTHER PUBLICATIONS

Gaku No Iyumi, "Medical Treatment of Viral Infectious Disease of Immunocompromised Patients by Infusion of Ex Vivo Activated T Cells", Weekly Journal of Clinical and Experimental Medicine, vol. 181, No. 6, May 10, 1997 (Translation).
Kei Numazaki et al., "Adoptive Immunotherapy for Interstitial Pneumonia Associated with Cytomegalovirus Infection", Clinical Infectious Diseases, vol. 25, No. 5, pp. 1246-1247, Nov. 1997.
Korcakova et al. (Folia Biologica, 24:32-38 (1978)).
Eren et al., Immunology, 93:154-161 (1998).

*Primary Examiner* — Michail Belyavskyi
(74) *Attorney, Agent, or Firm* — Browdy and Neimark, PLLC

(57) ABSTRACT

HLA matched activated lymphocytes in mononuclear cells separated from peripheral blood or umbilical cord blood are proliferated and activated. After separating and collecting, the HLA matched activated lymphocytes are employed as the main component of a composition for promoting survival of transplanted hematopoietic stem cells. The obtained composition is widely usable in, for instance, prevention of survival failure of transplanted hematopoietic stem cells and therapy for promoting the survival thereof. Although the dose of the composition varies depending on the age, conditions, etc. of a patient, a humanized antibody is administered in a dose of from 0.2 to 20 ml/kg/day to mammals including humans. The composition is administered by intravenous injection either once a day (single administration or continuous administration) or intermittently once to 3 times in a week or once in 2 or 3 weeks.

3 Claims, No Drawings

METHOD FOR PRODUCING A COMPOSITION FOR PROMOTING SURVIVAL OF TRANSPLANTED HEMATOPOIETIC STEM CELL

CROSS-REFERENCE TO RELATED APPLICATIONS

The present application is a divisional of application Ser. No. 12/556,162, filed Sep. 9, 2009, now abandoned, which is a divisional of application Ser. No. 10/559,448, filed Jul. 5, 2006, now abandoned, which is a 371 national stage application of PCT/JP04/07164, filed May 26, 2004, and which is incorporated herein by reference.

TECHNICAL FIELD

The present invention relates to a composition for promoting survival of transplanted hematopoietic stein cells that is employed for improving survival failure, which is especially a problem in transplantation of hematopoietic stem cells, disadvantage of delaying production of antibodies or immunocompromised condition, or for decreasing a risk for various types of infectious disease or relapse of cancers after survival, a kit for obtaining the composition, a method for promoting survival of the transplanted hematopoietic stem cells, and a human monoclonal antibody which is employed in therapy for various human diseases and a method for producing the human monoclonal antibodies or human polyclonal antibodies.

TECHNICAL BACKGROUND

Because cell transplanted patients, especially hematopoietic stem cell transplanted patients are in danger of a crisis of various types of infection or relapse of cancers, a lot of studies for corresponding to them have been carried out. Sekine who is one of the inventors of the present invention previously reported that lymphocytes could be propagated by using immobilized anti-CD3 antibodies and, interleukin 2, and the propagated autologous lymphocytes thus had an antineoplastic effect (JP 03-80076 A1).

Besides, it has already been reported that the autologous lymphocytes propagated with the anti-CD3 antibodies and interleukin 2 are effective to virus infections in congenital immunodeficiency patients [Kimiya ITO, Teruaki SEKINE; IGAKU NO AYUMI, Volume 181, NO. 6, Page 426 to 427 (1997)]. Furthermore, in a field for hematopoietic stem cell transplantation, when some of major HLA which consist of four loci, A, B, C and DR and further loci DQ and DP are matched between a patient and donor, a bone marrow transplantation or a blood transfusion can be carried out.

Moreover, since Kohler and Milstein developed the cell fusion technique in 1975, various monoclonal antibodies are produced and applied to an analysis, measurement, a diagnosis and therapy. Almost of the monoclonal antibodies reported by now are derived from animals, and especially mouse-derived, and obtained by immortalizing antibody producing cells from immunized animals by cell fusion. The monoclonal antibody is considered as an attractive drug carrier because it is uniform in an antibody subclass, is higher antigen specificity and has very small clearance, so that new Drug Delivery System (DDS) with a monoclonal antibody has been investigated.

DISCLOSURE OF THE INVENTION

Problems to be Resolved by the Invention

However, even if autologous lymphocytes propagated with anti-CD3 antibodies and interleukin 2 are effective to an antitumor effect or a viral infection in a congenital immunodeficiency patient, it does not mean a stage in which satisfactory effect can be necessarily expected with it. Although a bone marrow transplantation or a blood transfusion is carried out when some of major HLA loci are matched, a risk to develop a fatal side effect in a bone marrow transplantation or DLT treated patient according to mismatch in rest of HLA, namely Post Transfusion-Graft versus Host Disease (hereinafter, abbreviated as "PT-GVHD") is still existed.

Furthermore, also in the monoclonal antibodies, when animal-derived antibodies which are obtained by sensitizing antigens to the animals as described above are administrated to humans, it is difficult to use them regularly as a remedy because the antibodies themselves indicate immunogenicity. In order to avoid the immunogenicity, a method that the antigenicity can be decreased by means of a method such as to fragmentize the monoclonal antibodies originated from animals to Fab2, or F(ab)'2, to chimerarize with human antibodies, or to humanize, or a method that humanized antibody cell lines are established with a antibody producing cell obtained from the real patient or human lymphocytes sensitized in vitro and so on are examined.

However, because the respective methods have problems in the points of a residual of antigenicity, difficulty of establishing human antibody producing lines, decrease of capacity of antibody production during cell culture and so on, it is strongly desired to develop a method for establishing human antibodies easily and efficiently by the other procedure. Besides, the polyclonal antibody also has problems similar to in the monoclonal antibody, so that various methods are examined in order to medicate them to human safely and efficiently.

A Means for Resolving the Problem

The inventors in the present invention succeeded in preparing HLA matched activated lymphocytes possible to improve survival of stern cells to a transplanted patient with that cells whose HLA is identical to transplanted hematopoietic stem cells are stimulated and propagated by interleukin 2 and anti-CD3 antibodies and then they are given to the patient, resulting from diligent studies for the purpose of developing a medicament and a method for improving the survival of transplanted cells, especially hematopoietic stem cells.

Furthermore, the inventors succeeded in producing human monoclonal antibodies efficiently by sensitizing antigens as giving human activated lymphocytes to immunocompromised mouse in which human hematopoietic stem cells are transplanted. Namely, if an embodiment of a primary invention is mentioned, an invention according to claim 1 relates to a composition for stabilizing survival of transplanted hematopoietic stein cell whose main component is HLA matched lymphocytes produced by separating and collecting them after propagating and activating HLA matched lymphocytes in mononuclear cells separated from peripheral blood or umbilical cord blood.

Besides, an invention according to claim 4 relates to a method for producing a composition for stabilizing survival of transplanted hematopoietic stem cells, comprising a process for separating mononuclear cells from peripheral blood or umbilical cord blood including HLA matched lymphocytes, a process for propagating and activating the HLA matched lymphocytes in the separated mononuclear cells, and a process for separating the propagated and activated HLA matched lymphocytes and preparing remedy having them as a main component.

Furthermore, an invention according to claim 7 relates to a kit for obtaining the composition for stabilizing survival of transplanted hematopoietic stem cells comprising an implement for separating HLA matched lymphocytes from peripheral blood or umbilical blood, an implement for propagation and activation comprising either/both culture medium including interleukin 2 or/and an anti-CD3 antibody solidified flask, and an implement for taking out the HLA matched lymphocytes cultured by the implement for propagation and activation. Moreover, an invention according to claim 8 relates to human monoclonal antibody producing cell lines collected by a method such that HLA matched activated lymphocytes are given before or after transplanting to mammals, antigens are sensitized after stabilization of survival, and the antigen sensitized lymphocytes are established or separated from the mammals, or a method for gene separation or expression, etc.

Furthermore, an invention according to claim 9 relates to a method for producing human monoclonal antibody producing cell lines collected by a method that human hematopoietic stem cells are transplanted to mammals which are severe combined immunodeficiency mice such as SCID mice, and further antigens are sensitized after the survival by giving HLA matched activated lymphocytes before or after the transplantation, the antigen sensitized lymphocytes are established or separated from the mammals, or a method for gene separation or expression, etc.

Effect of the Invention

As mentioned above, the present invention relates to remedy for preventing survival failure and promoting survival after transplantation of hematopoietic stem cells characterized that it includes HLA matched activated lymphocytes whose main component is HLA matched propagated/activated lymphocytes or propagated donor lymphocytes, so that it can be used widely for promoting the survival of the stem cells at transplantation. As well as it can be used for promoting the survival of the stem cells, it can also be used for promoting survival of various internal organs, and antibodies which have specificity and high binding affinity with the antigen can be obtained by transplanting human hematopoietic stem cells to mammals and giving HLA matched propagated/activated lymphocytes and immunogens. Besides, the human monoclonal antibodies can be produced efficiently by using the cells producing the antibodies. Moreover, it can be used widely as screening of the remedy such as anti-virus medicament, anti-cancer medicament and anti-hypertension medicament by transplanting the human hematopoietic stem cells and using the mammals which are transplanted with HLA-identical propagated/activated lymphocytes.

BEST MODE FOR CARRYING OUT THE INVENTION

Hereinafter, concrete contents of the invention are explained.

[HLA Matched]

HLA matched in the present invention is matching by not less than three loci among several primary HLA components such as 4 loci A, B, C, DR, and further DQ and DP.

[Collecting Lymphocytes]

HLA matched lymphocytes for propagating and activating can be collected by a following method. Namely, HLA matched activated lymphocytes can be prepared from lymphocytes which are collected from peripheral blood, lymph node, bone marrow, or various body fluid of a donor of hematopoietic stem cells. Though HLA matched activated lymphocytes can be prepared by cultivating the hematopoietic stem cells, it is extremely desired in respect of efficiency that lymphocytes prepared from the peripheral blood of the donor is used as a material. Besides, activated lymphocytes whose HLA is matched to the donor of hematopoietic stem cells in at least three loci are prepared, and it is possible to use them.

It is simple and therefore preferred to collect blood from vein in upper limb of the donor as a method for collecting blood, but anything containing lymphocytes can be used as a material. Besides, umbilical cord blood can be used as a material.

Only a small quantity of blood in a range between 0.001 ml and 500 ml is preferred as a quantity of collecting blood, and especially collecting blood in a range approximately between 10 ml and 100 ml is preferred. Furthermore, heparin or citric acid can be added into the collected blood so as to prevent coagulation.

[Incubating, Propagating and Activating of HLA Matched Lymphocytes]

The collected HLA matched lymphocytes are incubated, propagated and activated by following processes.

Note that the term "incubation" of the collected lymphocytes means that tissue cells are propagated (incubated) artificially by placing a small piece of cell tissue in a culture medium containing necessary nutrients for the cells to survive, and the term "propagation" of them means that the tissue cells are increased quantitatively in vitro by the above-mentioned incubation artificially. Furthermore, the term "activation" of them means that resting functions are regulated so as to work actively by stimulating the cells with addition of a propagating agent or an activating agent into the culture medium, and further concretely, means that a property of prevention of the failure of the survival and promoting the survival are given.

Propagation of HLA matched activated lymphocytes can be carried out by conventional cultivation of lymphocyte cells, and the cultivation is not limited especially, but for instance, as disclosed in JP 03-80076 A1, it can be carried out by using either interleukin 2 or anti-CD3 antibodies alone or by using them in combination to cultivate them. In this case, from the point of view of improving propagation efficiency, it is preferred to incubate under existence of both interleukin 2 and anti-CD3 antibodies.

Not only the above mentioned interleukin 2 or anti-CD3 antibodies but also various cytokine, anti-CD28 antibodies or various mitogens can be used. In this case, any matters which have a function for propagating and activating lymphocytes can be used. In addition, interleukin 2 used in this case can be a marketed product, and preferably used so as to achieve a 1 to 2000 U/ml concentration in the culture medium solution.

Interleukin 2 can be dissolved and used in any medium solution widely used for cell culture, such as water, saline, Dulbecco's phosphate buffered saline, RPMI-1640, D'MEM, IMDM and AIM-V. Once interleukin 2 is dissolved, it is preferred that the solution is stored in a refrigerator so as to prevent decrease of activity. It is to be noted that any culture medium solutions used in this case are not especially limited if they are available to cultivation of the lymphocytes, and for instance, an organism derived materials such as a blood serum or a synthetic medium adding amino acids, vitamins and nucleic acid into balanced salt solution can be used, and further desirable examples of them include RPMI-1640, AIM-V, D'MEM, IMDM and the like, and especially RPMI-1640 is preferred.

As the culture medium used in this case, a culture medium containing normal human serums is preferred because it is superior in propagation, and marketed culture mediums can be used. In addition, instead of the human serum, a fetal calf serum can also be used. Alternatively, a serum-free medium can be used. The incubation can be achieved by adopting any of the generally practiced incubation methods, e. g., inside a $CO_2$ incubator. It is preferred that $CO_2$ concentration is in a range from 1 to 10%, especially in a range from 3 to 7%, and that temperature is in a range from 30 to 40° C., especially in a range from 35 to 38° C.

The number of days for this incubation are not limited, but an stimulation signal from anti-CD3 antibody is assumed to be transmitted to lymphocytes, it is ideal from the point of view such as to stimulate stably the cells with anti-CD3 antibody and to increase the incubation efficiency that this incubation for approximately 2 to 30 days, especially for 3 to 21 days is preferably carried out. In order to increase the incubation efficiency, it is more preferred to observe the condition of cells under a microscope, to count the number of the cells and to add the culture medium as necessary. It is to be noted that while no marked increase in the number of cells is observed for the initial 1 to 2 days after the incubation started, cell propagation is first observed around the third day and once the cells start to propagate properly and the color of culture medium changes from orange to yellow.

Note that an additional loading volume of the culture medium is preferably in a range approximately between 0.1 and 5 times relative to the volume of the culture medium prior to addition. Furthermore, additional loading is preferably carried out once every 1 to 7 days, especially once every 3 to 5 days in order to prevent unfavorable condition of the cultivation and decrease of activity of interleukin 2. Moreover, after the incubation with anti-CD3 antibodies, the incubation process can be allowed to continue without stimulation with anti-CD3 antibodies. Namely, the incubation can be continued in a culture vessel without solidified anti-CD3 antibodies, e. g., an incubating flask, a roller bottle, or a gas permeable bag for cultivation until the administration The incubation of the lymphocytes under these conditions is preferably carried out under the same conditions as that of the incubation under the presence of anti-CD3 antibodies except that there is no stimulation by anti-CD3 antibodies, and further it is more preferred in workability, cost performance and safety to adjust concentration of the human serum and to use a serum-free medium as necessary.

At the incubation, for instance, the umbilical cord blood or the mononuclear cells are floated in a culture medium containing interleukin 2, and the resulting solution is placed in a cultivation vessel solidified anti-CD3 antibodies, so that the cultivation can be started. Furthermore, in this case, the efficiency of lymphocytes' propagation or activation is more improved by adding and using various cytokines or mitogens into the culture medium as the need arises. It is to be noted that anti-CD3 antibodies used in stimulation of the lymphocytes can be produced in an animal or in cells by using purified. CD3 components, but marketed OKT-3 antibodies (manufacturer: Ortho Pharmaceutical) which are outstanding in stability and cost performance can be used.

However, besides this, antibodies are not especially limited if they can promote the propagation and activation of the lymphocytes, for instance, anti-CD28 antibodies can be used. Anti-CD3 antibodies are preferably used in solid phase from the point of view of propagation efficiency and operability of the lymphocytes. A cultivation vessel which the antibodies are solidified on its surface is an incubation container constituted of a material such as glass, polyurethane, polyolefin or polystyrene. In this case, a marketed plastic sterilized culture flask and the like can be used because it is easy to obtain it, and further a size of it can be selected as appropriate.

In addition, solidification of the antibodies can be carried by adding diluent of anti-CD3 antibodies into the cultivating vessel, and for instance, by leaving the vessel in a stationary state for 2 to 24 hours at between 4 to 37° C. It is preferred that when anti-CD3 antibodies are solidified, anti-CD3 antibodies are diluted to a concentration of 0.1 to 30 µg/ml in a physiological buffer solution such as sterilized Dulbecco's phosphate buffered saline. After the solidification, the vessel is possible to be stored in a cold room or in a refrigerator (4° C.) until use and, in this case, the liquid can be removed at the time of use and if necessary, the vessels can be used by washing them with a physiological buffer solution such as Dulbecco's phosphate buffered saline at room temperature.

The HLA matched peripheral blood-derived activated lymphocytes obtained by propagation as above mentioned can be processed or formulized as follows, and this can be used over wide range of applications as a means for biodefence such as a remedy for the preventing failure of the survival or the promoting survival after transplantation.

Furthermore, in the case that there is a risk for any side effects such as PT-GVHD (Post Transfusion—Graft versus Host Disease) at transplanting, it is effective that prepared peripheral blood originating activated lymphocytes are processed with anti-CD4 antibodies and the like and used with preparing so as to be a cell group including CD4+ cells mainly.

When a risk for a side effect such as GVHD is little or when an antineoplastic effect or an antiviral effect in addition to the preventing failure of the survival or the promoting survival is expected, it is effective that cell population including CD8+ cells is used. Besides, in this case, it can be used in therapy as cell population preparing a content of the CD8+ cells suitably.

[Agents Having HLA Matched Activated Lymphocytes as its Main Component]

The HLA matched activated lymphocytes having more propagated cells as a main component can be prepared by adding various medical components to them, for instance, so as to use them as a therapeutic formulation for the preventing survival failure or the promoting survival by preparing in a mode in which they are suspended in saline for transfusion containing human albumin. It is to be noted that "formulation" as described here means every material having a biodefensive function which contains the active lymphocytes as its main component, and any forms are not limited if they include HLA matched activated lymphocytes.

For instance, it is available that a formulation that HLA matched activated lymphocytes are suspended in an suitable solution may be also suitable, and in this case, it is preferred that a formulation is HLA matched activated lymphocytes, especially suspended in saline for transfusion containing the human albumin, but it is not limited by this example.

In addition, in this case, to prepare formulation containing HLA matched activated lymphocytes as a main component, peripheral blood or umbilical cord blood can be cultured in vitro or mononuclear cells can be propagated in vitro after separating from peripheral blood or umbilical cord blood. Besides, HLA matched activated lymphocytes contained in the formulation according to the present invention may be the cells that various genes are introduced or that original genes are deleted or modified.

[Preparation Kit of a Formulation Containing HLA Matched Activated Lymphocytes as a Main Component]

Besides, HLA matched activated lymphocytes according to the present invention can be used as a formulation with the component of it as an independent reagent, a kit combining culture medium containing interleukin 2 and anti-CD3 antibody solidified flask as components is made, and it is easy to prepare the formulation according to the present invention by using this kit.

It is to be noted that the culture medium used in this case can be added in advance into anti-CD3 antibody solidified flasks separately, and further they can be cryopreserved. Thus, by producing a kit combined at least two components as a plurality of reagents and by using it when activated lymphocytes are needed, it can be carried out more easily to prepare the formulation according to the present invention.

HLA matched activated lymphocytes possible to be used in any form of the present invention or formulation including them are cryopreserved, and then they can be used in preventing survival failure or improving survival such as promoting survival as the need arises. Besides, HLA matched activated lymphocytes can be cryopreserved by a method as follows.

In HLA matched activated lymphocytes to be preserved, the concentration of them to suspend in a preservation liquid can be selected availably due to the sizes of them, preferably they are suspended in the cell preservation liquid at the concentration in a range from $1\times10^3$/ml to $1\times10^{10}$/ml to be cryopreserved, and more preferably they are suspended in the preservation liquid at the concentration in a range from $1\times10^5$/ml to $1\times10^8$/ml to be cryopreserved. The preservation liquid to be used in this case is not to be limited especially, but it is preferred for the sake of convenience that it can be used in a range from 0.1 ml to 1,000 ml, especially from 0.5 ml to 100 ml.

When they are cryopreserved, not only marketed preservation liquid but also preservation liquid in house can be used. As an ingredient of the preservation liquid, suitable buffer solution or solution including serums, proteins, macromolecular substances such as polysaccharide or dimethyl sulfoxide (may be abbreviated to DMSO) can be used, but all of the listed materials are not always used due to the preserved HLA matched activated lymphocytes. Therefore, if the preservation liquid could preserve HLA matched activated lymphocytes in it, the compositions of them are not limited. Thus, HLA matched activated lymphocytes are suspended in the suitable preservation liquid and cryopreserved at low temperature.

[Dosage]

Furthermore, the dose of the formulation containing HLA matched activated lymphocytes as its main component can be adjusted suitably in accordance with a condition of the transplanted patient or the objective of the therapy, the standard dose administered under standard condition is in a range from $1\times10^2$ to $1\times10^9$ lymphocytes relative to 1 Kg of body weight. Besides, the dose is preferably not less than $1\times10^3$ lymphocytes/kg in order to increase the effect further, and even if the dose exceeds $5\times10^8$ lymphocytes/kg, the further effect is not expected, so that the best dose is in a range between $1\times10^3$ and $5\times10^8$ lymphocytes/kg.

[Forms and Methods of Administration]

Furthermore, as forms of administration of the formulation as described above, liquid such as an injection and a drip is preferred, and it is more preferred to suspend the cells in saline containing 0.01 to 5% of human blood serum albumin as the form of the injection or the drip. An intravenous drip or an intravenous, intraarterial or local injection is preferred as a way for administration. As a volume of solution to be administered depends on the way for administration or the administered region, it is preferred that the volume is usually in a range between 1 and 500 ml and that the solution includes cells of the above described lymphocytes dosage. Furthermore, the frequency of such administration is preferably once a day to once a month, and further it is necessary that the number of administration is at least more than once.

[Manufacturing Process of Human Monoclonal Antibodies]

Next, we explain about an effective manufacturing process for human monoclonal antibodies by using animals, which antibodies are safe and have good survival in animal after the cell transplantation. Concretely, HLA matched activated lymphocytes are administered before or after transplantation to an animal under immunocomprimised condition, the antigens are immunized after stabilizing the survival, and then antigen sensitized lymphocytes are established or collected from the animal by a method such as the gene selection or gene expression.

As explaining about an animal under immunocomprimised condition, a cow, a house, a sheep, a goat, a rabbit, a guinea pig, a rat, a chicken, a duck and the like are listed up as an example, especially a mouse is preferred in management or handling easily. A SCID (severe combined immunodeficiency: hereinafter saying SCID) mouse among the mice is known as a mouse with extremely lower blood concentration of immunoglobulin than C.B-17 mouse which is an allotype congenic lines of BALB/c mouse in immunoglobulin (Ig) heavy chain gene, and presents severe combined immunodeficiency.

Thus, because of deficiency of mature T and B cells in the SCID mouse, it is known that SCID mouse has some of abnormal recombinase concerning gene rearrangement indispensable for expression of immunoglobulin molecules, and especially that there is abnormality in substrate specificity of the recombinase. Therefore, self-antibodies in the SCID mouse are hardly produced. Although no antibody-dependent cell mediated cytotoxicity (ADCC) is observed in this mouse, the function of antigen presenting cells or NK cells are normal.

By applying the properties of the SCID mouse different from a nude mouse, a TC mouse (Transchromo mouse) or a mouse in which immune function are disrupted by irradiation, SCID mouse is used in the analysis of effect of anticancer drug against xenogenically transplanted various tissue or tumors, or in production of models for infectious disease specific to human such as acquired immunodeficiency syndrome (AIDS) or Epstein-Barr virus (EBV). It is known as SCID-hu mouse which human foetal thymus and a small piece of embryonic liver is transplanted intrasubcapusular of kidney with maintaining organ structure and hu-PBL-SCID mouse which human peripheral blood lymphocytes are transplanted into intraperitoneal.

The latter can induce human antibodies specific to tetanus toxin or C-antigens of hepatitis B virus by immunizing the mouse. Besides, because of expectable application to an autoimmune disease model and so on, SCID mice can be model animals indicating human disease pathology, which can not be obtained from the other animals, by transplantation of various xenogenic tissue, especially human tissue.

Accordingly, in the present invention, these SCID mice are used as a mass production means of human monoclonal antibodies. The SCID mice used in the present invention are usually 5- to 15-week-old, preferably 8- to 12-week-old.

Concretely, the human lymphocytes from $1\times10^7$ to $5\times10^8$, preferably approximately $1\times10^8$, such that human lymphocyte fractions produced from peripheral blood, cerebrospinal fluid, umbilical cord blood or immune system tissue and the like such as the spleen including human stem cells by a conventional process are suspended in solution which does not influence to cells and a living body such as physiological saline and phosphate buffer physiological saline (PBS) are transplanted to the SCID mouse intraperitoneally or intravenously.

In this case, as one of transplanting procedure, a method that transplanting cells are encapsulated in an immunologically isolated membrane and then transplanted into intraperitoneal may be adopted. In this method, because the transplanted cells are not in contact with host cells by the membrane after transplanting, GVH (graft-versus-host) reaction is prevented, so that efficient production of antibodies against targeted antigens are increased.

Recovering antigen specific human antibody producing cells is usually carried out in 7 days through 60 days after the transplantation, preferably 7 days through 28 days, and especially preferably 25 days through 28 days. Especially from the point of collection efficiency, it is preferred that increasing concentration of a human antibody and increasing titer of antigen specific human antibody are examined by collecting a proper volume of blood from an orbit of the SCID mouse every week from about seventh day after the transplantation.

In measurement of the human antibody concentration and the antigen specific human antibody titer, there are various methods such as an enzyme immunoassay (hereinafter, abbreviating EIA), a passive hemagglutination reaction technique, a fluorescent antibody technique, an Ouchterlony method, a dot immunoassay method and the like, but in the case that the antigen is a soluble form, the EIA using an immuno plate (for instance, Nunc Co. Ltd, made in Denmark) that conventional anti-human immunoglobulin or the aimed antigens are solidified is suitable. According to these methods, the human antibody producing cells can be recovered from the SCID mouse indicating a higher antibody quantity and a higher antibody titer.

Though the antibody producing cells can be collected from each of the SCID mouse's organs, above all, it is very profitable in the points of a recovery factor and a purity to collect from the lymph node. The human monoclonal antibody producing cells obtained in the present invention are very excellent in comparison with conventional induction of human antibody producing cells in vitro in the point of the antibody titer measurement, Plaque method or an immunofluorescent assay, and further it is very excellent to obtain the human monoclonal antibodies.

As a concrete method for collecting and purifying of the human antibody producing cells according to the present invention, the following method is used. Firstly, each of the internal organs is minced into a single cell physically. if the content of the antibody producing cells in cells collected, from the internal organs is larger, the collected cells are used to establish the antibody producing cells as it is. However, when the purity of the antibody producing cells is lower, for instance when cells of the SCID mouse are contaminated into considerably, the purity of the antibody producing cells is increased due to purifying by a density gradient centrifugation, a panning method using the antigens, a cytolytic method using anti-mouse cell antibodies and complements for removing the SCID mouse derived cells or an affinity column method using conventional anti-human B cell antibodies.

Next, the purified human antibody producing cells are established by the following method. As the method for established cell line, an Epstein-Barr virus transformation method and a cell fusion method by fusing with self-proliferative cells can be mainly listed up. In the transformation by the Epstein-Barr virus, the Epstein-Barr virus prepared by a conventional method, for instance 0.5 through $5\times10^7$/ml of the human antibody producing cells are suspended into a propagation medium containing 1:10 to 10:1 of culture supernatant fluid of the cell line B95.8 and the like, and are incubated at 37° C. for 1 hour through 18 hours.

After the incubation, the cells are centrifuged at room temperature, suspended to culture medium and added 0.1 ml each of cell suspension at concentration of $1\times10^6$/ml through $1\times10^5$/ml to each well of a 96 wells plate. Furthermore, the cells are cultivated in an incubator such as a $CO_2$ incubator at 37° C., the culture supernatant fluid in a well in which the transformed cells are cultivated for 7 days through 30 days is collected, and then the only transformed cells producing the targeted antibodies are selected by using a suitable screening system such as the above mentioned EIA.

The cell fusion is performed by a conventional method and is that polyethylene glycol (hereinafter, abbreviated PEG), Sendai virus and the like are used as a fusion agent. Besides, an electrofusion method may be used, but PEG is preferably used. PEG with mean molecular weight of 1000 to 9000 is used, and especially it is preferred to use PEG 4000 or PEG 6000.

The concentration in this case is used in a range from 10 to 80%, preferably from 40 to 50%. As a parent cell line using in cell fusion, every parent cell line can be used, but a cell line with drug selection marker is preferred. Besides, preferably human myeloma and human lymphoma cell lines, especially preferably human lymphoma AC-33 cell, and LICR-2 cell or SKO-007 cell as a human lymphoblastic cell line are listed up. The antibody producing cells obtained from SCID mice and suitable cell lines which are preferably human myeloma and human lymphoma cell lines and especially preferably human lymphoma AC-33 cell are washed with a serum-free culture medium. The antibody producing cells and the parent cells are mixed usually in the ratio of 1:1 through 10:1 are centrifuged at 700 rpm at room temperature for 5 minutes, and the cells are recovered as pellets.

Furthermore, the cell pellets are loosened as warming in an incubator at 37° C., and then pre-warmed PEG solution is added gradually into and mixed with the cell pellets. Usually, the PEG solution is added at 1 ml per $10^8$ cells, but the volume of it may be adjusted as the need arises. Next, pre-warmed culture medium is added dropwise in the cell suspension to decrease PEG concentration. Usually, 1 through 30 ml of the culture medium is added in approximately 10 minutes.

Furthermore, the cells are collected by centrifugation at room temperature, they are left in a culture medium containing 10% fetal calf serum (hereinafter, abbreviated FCS) as the parent cells at cell concentration of 1 through $5\times10^5$/ml overnight, and then a culture medium (HAT culture medium) containing HAT and 10% FCS is added to them. Besides, for omitting this step of operation, the cells may be suspended directly in HAT culture medium after the cell fusion. Then, the culture medium is changed several times during two through three weeks.

A method for changing the culture medium is to remove a part of culture medium ranging from 0.1 to 0.2 ml and to add the same volume of freshly prepared HAT medium to the culture medium. If appearance of hybridoma is observed, the hybridoma producing the targeted antibodies are selected by a suitable screening system such as the above mentioned EIA as soon as possible. Cloning is carried out in the obtained hybridoma by a suitable method immediately.

As a liquid culture medium using in the cell culture, Daigo's T medium (NIHON PHARMACEUTICAL Co. LTD.), Dulbecco's modified Eagle medium, RPMI-1640 medium, Iscove's modified Dulbecco's medium and the like can be selected. In the case of the transformation method by Epstein-Barr virus, the culture medium which contains about 20%

FCS is used. In the case of the cell fusion method, in which contains 10 through 15% FCS. The human monoclonal antibodies can be obtained from the antigen specific human antibody producing cell lines by a conventional method.

For instance, by inoculating the human antibody producing cell line into intraperitoneal of SCID mouse, ascites fluid containing the monoclonal antibodies similar to mouse hybridoma at high concentration can be obtained. The monoclonal antibodies producing cells can be cultivated in large volume by using a suitable serum-free culture medium such as GIT medium (NIHON PHARMACEUTICAL CO., LTD.), HB104 (HANAMEDIA CO., LTD.) and Hybrity 1 (Nihon Yakuhin Kaihatu Co., Ltd). Large amount of highly purified human monoclonal antibodies can be obtained from the above ascites or culture supernatant by combining suitable conventional purification methods.

In this case, for instance the solution including the antibodies is centrifuged and then the supernatant fluid of the solution is salted out. Usually, ammonium sulfate is used on this occasion. After dissolving the obtained protein sediment to a suitable buffer solution and dialyzing it, the targeted Human monoclonal antibodies can be separated and purified by a column chromatography (a DEAE ion exchange column, a hydroxyl apatite column, a gel filtration, a protein A column, a protein G column, and the like) or an immuno affinity chromatography and the like. The purity of the purified human monoclonal antibodies by these methods is over 99.9%, so that they are administrable to the human as a medicament.

Besides, there are IgA, IgM, IgG, IgD and IgE in a class of the antibody, and further the IgG class has 4 subclasses of IgG1, IgG2a, Ig2b, IgG3 in the case of the mouse (IgG1, IgG2, IgG3, IgG4 in the case of the human). When the antigen is given to the animal, IgM or IgG classes of antibodies are produced in most cases. IgG whose molecular weight is approximately 160,000 has dimeric structure and is relatively easy to handle. Compare to IgG, IgM is a larger molecule with approximately 900,000 molecular weight and exists in complicated pentameric structure joined with J-chain, so that there are defects such that purification is difficult, that preservation is difficult because of its easily aggregating character, that it is difficult to produce Fab because it is easy to inactivate due to partial degradation by a proteolytic enzyme, and that there are many cases that binding activity is lost when chemical modification such as to conjugate with anticancer drug or a toxin chemically are carried out.

About which is superior in a curative effect to the cancer, the monoclonal antibodies in IgG class or the monoclonal antibodies in IgM class, Bernstein et al examine in detail by using the monoclonal antibodies in IgG class and IgM class to Thy-1 antigens of the lymphocytes. [Monoclonal Antibody, R. H. Kennet, T. J. McKearnand, K. B. Bechtol editing, Plenum Press 1980, P. 275]

According to it, as a result of comparing monoclonal antibodies in IgG class with monoclonal antibodies in IgM class with reactivity of the same strength to Thy-1 antigen positive lymphocytes, though the monoclonal antibodies in IgM class was superior in a complement dependent anti-tumor effect in vitro, the significant anti-tumor effect was recognized in the monoclonal antibodies in IgG class in the anti-tumor effect in vivo which was examined by using a tumor bearing mouse, but the anti-tumor effect was not recognized in the monoclonal antibodies in IgM class.

Furthermore, when the isotopes labeled monoclonal antibodies were injected in the mouse and the half-life in blood was examined, it was found that the half-life in blood of the monoclonal antibodies in IgM class was much shorter than the monoclonal antibodies in IgG class. Thus the result indicates that the monoclonal antibodies in IgG class are preferred as the monoclonal antibodies used in human clinical use.

The humanized antibodies of the present invention can be used independently or together with at least not more than one kind of additive allowed upon the preparation. For instance, a suitable medical composition can be achieved by dissolving the humanized antibodies in a solution such as saline, glucose, lactose and mannitol, or powder-injection can be produced by lyophilizing the humanized antibodies by conventional method and adding sodium chloride into the lyophilized antibody, and further the present medical composition can contain additional agents known in a pharmaceutical field, for instance, pharmaceutically acceptable salts as the need arises.

Besides, dosage of the composition according to the present invention is varied depending on the age, conditions and the like of a patient, but the humanized antibodies are administered in a dose of from 0.2 to 20 mg/kg/day to mammals including humans. The composition is administered by intravenous injection either once a day (single administration or continuous administration) or intermittently 1 to 3 times in a week or in 2 or 3 weeks.

[A Method for Producing Genetically Engineered Human Monoclonal Antibodies from Human Monoclonal Antibody Producing Lines]

Genes coding the human monoclonal antibody are extracted from the human monoclonal antibody producing cell line of the present invention by a way in the genetic engineering, they are inserted into expression vectors, they are introduced in host cells, and then the human monoclonal antibodies producing transformant can be obtained.

The genes used in the present invention are obtained by a usual method and the other various methods, and can be cloned. [edited by L. G. Davis et al: Basic methods in Molecular Biology, Elsevier publication, New York, 1986; and J. Feder et al. American Journal of Human Genetics, 37, 635 (1985)]

A mRNA used in the present invention is also prepared by conventional method used usually. cDNA is prepared from it, and it can be cloned. [Edited by J. Sambrook et al: Molecular Cloning—A Laboratory Manual—, Cold Spring Harbor Laboratory Press published, New York, 1989]

For instance, the genes can be obtained from genomic libraries by conventional procedure. Namely, genes of the cells are prepared by a standard method. For instance, after proteinase K treatment of the cells under presence of Sodium Dodecyl Sulphate (SDS), phenol extraction are performed, and further after DNase-free RNase A treatment, phenol extraction are performed, so that the genes are obtained. [Edited by Masami Matsumura: Labo Manual Gene Engineering: Maruzen Co., P 59 (1988)]

Next, if the targeted genes contain immunoglobulin variable region, the genes are only isolated by a standard method, namely genomic DNA is fragmentized with restriction endonuclease, inserted in an appropriate recombinant DNA cloning vector, and screened against the specified DNA sequence in the present invention by using a radio labeled probe or enzyme labeled probe. Because DNA obtained from the genes generally also includes intron, non coding region, the DNA is modified by deletion or replacement of DNA by a conventional method. [W. Kramer et al: Nucleic Acids Research, 12, 9441 (1984), and T. A. Kvnkel: Proceedings of National Academy of Science USA, 82, 488 (1985)]

DNA that encodes the sequence of the polypeptide of variable region of immunoglobulin light and heavy chain of the human monoclonal antibody in this invention can be obtained from cDNA library by conventional methods. [H. Okayama et al: Molecular and Cellular Biotechnology, 2, 161 (1982)]. Namely, the cells are homogenized in guanidine thiocyanate solution, subsequently RNA pellet is precipitated by ultra-centrifugation on cesium trifluoroacetate-EDTA density gradient and mRNA as poly (A)$^+$-RNA further purified on oligo-dT column.

By using poly (A)$^+$-RNA as a template, a first strand cDNA is reverse-transcribed by a conventional process using an oligo-dT primer, a random primer or a specific primer in DNA sequence of antibody gene, and further a second strand cDNA is synthesized by using the first strand cDNA as a template. [Edited by M. Matsumura: labo Manual Gene Engineering; Maruzen Co., P. 70. P. 77 (1988)]

The cDNA obtained by thus conventional method is inserted in a suitable cloning vector, cDNAs coding the variable region are screened in the obtained clones with an appropriate prove for cDNA coding the variable region. After isolating the targeted clones only, cDNA can be handled basically in same way as the genomic DNA. Besides, DNA coding variable region of immunoglobulin light chain and heavy chain of the human monoclonal antibody can be obtained by amplifying specially with polymerase chained reaction by a conventional method. [R. Orlandi et al: Proceedings of National Academy of Science USA, 86, 3833 (1989)]

The DNA coding variable region of light chain and heavy chain can be chemically synthesized by a conventional process. [N. D. Shina et al: Nucleic Acids Research, 12, 4359 (1984)] Even if an original codon is displaced by a degenerate codon, as long as same amino acid is coded when it is translated, it is not necessary that these synthesized DNA is the same as DNA obtained by cloning.

The DNA coding non-variable region of immunoglobulin light chain and heavy chain in the present invention can be cloned from genomic DNA and cDNA. Besides, they can be synthesized chemically. The polypeptide of light and heavy chain with lower immunogenicity can be obtained by selecting the DNA coding the non-variable region of human monoclonal antibody. The DNA coding the non-variable region of human monoclonal antibody can be obtained from human lymphocytes, for instance peripheral blood lymphocytes.

The DNA construct obtained thus can be inserted into suitable recombined DNA cloning vectors and recombined DNA expression vectors.
[Edited by Y. Gluzman: Eukaryotic Viral Vectors, published by Cold Spring Harbor Laboratories]

In the present invention, the DNA construct coding the polypeptide of light and heavy chain is transducted into suitable host cells as a part of the expression vector. Examples of the host cell expressing human monoclonal antibodies according to the present invention are preferably hybridoma, a CHO (Chinese Hamster Ovary) cell, myeloma, plasmocytoma, lymphoma and the like. Besides, it may be a plant-derived host cell.

[Preparation of Human Polyclonal Antibody]

Next, we explain about a method for efficient production of human polyclonal antibodies by using animals in which antibodies are safe and have good survival in animal after the cell transplantation. Concretely, HLA matched activated lymphocytes are administered before or after transplantation to an animal under immunocompromised condition, the antigens are immunized after stabilizing survival, and then antigen sensitized lymphocytes are collected from the animal by a method such as the gene selection or gene expression.

As explaining about an animal under immunocompromised condition, a cow, a house, a guinea pig, a rat, a chicken, a duck, and the like are listed up as an example, especially a goat or a rabbit is advantageous in point of simple management or easy handling. Besides, there are a large amount of polyclonal antibodies to be collected. Further, an amount of immunogen can be also set suitably in accordance with a kind of the animal and interval of immunization can be also set suitably Any method that immunization can be applied to a normal animal is selectable. For instance, the immunization can be carried out through any way such as subcutaneous, intraperitoneal, intravenous, intramuscular, or intradermal. It is desired that the immunogen is given together with a suitable adjuvant such as a marketed complete Freund's adjuvant, incomplete Freund's adjuvant, BCG, aluminium hydroxide gel and pertussis vaccine.

The human monoclonal antibodies or the human polyclonal antibodies contained by the present invention is extremely advantageous in point such that antigenicity is lower or absent when they are used in the field of various therapies and diagnosis that is planed to apply a substitute of antiserum against infectious disease or drug intoxication, as anti-idiotype antibody vaccine, as anti-adhesion molecules antibody in order to neutralize inflammation or as catalytic antibody.

In the cases that the antibodies according to the present invention are used concretely as a diagnostic reagents, they may be used as a suitable labeling substance such as enzymes, dyes and radioisotopes or labeling antibodies conjugated chemically or in a genetic engineering; and the antibodies according to the present invention are used as drug, for instance in the case that antigens are bioactive substance such as toxin, the antibodies which have preferably a neutralizing capacity to activity of antigens can be administrated independently or as a admixture with a suitable combined drug. The antibodies also can be administered for instance in therapies to the cancer, thrombosis and the like as a targeting antibody formulation conjugated with suitable agents by chemically or in genetic engineering.

Moreover, the human monoclonal antibodies or the human polyclonal antibodies according to the present invention are prepared as parenteral agents, preferably as injections, according to the usual ways independently or by mixing with a pharmacologically acceptable carrier, an excipient or a diluent after filtration and sterilization with a membrane filter and the like as the need arises, and then they can be used in therapies for various diseases by giving to the mammals (mice, rats, cats, dogs, pigs, cows, monkeys, humans and the like) subcutaneously, intravenously or intramuscularly and the like.

Besides, a medicament can be produced by dissolving the monoclonal antibodies or polyclonal antibodies of the present invention in a suitable solution such as a phosphate-buffer, a saline, a Ringer solution and the like, sterilizing according to the usual way for instance by an aseptic filter and sealing up them into ampoules. Furthermore, solid-state medicament can be produced by lyophilization of these liquid-type medicines according to the usual way. Furthermore, although the dose of the human monoclonal antibody or the human polyclonal antibody of the present invention varies depending on weight, age or sexuality of administration objects, or targeted diseases, symptoms or administration routes, they can be administered in a dose of from 1 µg to 1 mg/kg weight/a day as an immunoglobulin quantity once a day or a few times a day continuously or intermittently.

Embodiment NO. 1

Hereinafter, the present invention is explained due to the embodiment No. 1.

(1) <Preparation in OKT3 Solidified Flask (Middle) and (Large)>

Five ml of OKT3 solution prepared at 5 μg/ml in PBS(−) was put into a culture flask (middle) and 10 ml of OKT3 solution of was put into a large sized culture flask (large), so that the bottom surfaces of the flasks were evenly covered with the solution. They were preserved in a cold room just before using.

(2) <Collecting Lymphocytes from Umbilical Cord Blood for Transplantation>

The OKT3 solution in the OKT3 solidified flask (middle) prepared in the same way as the above item (1) was aspirated by suction. Ten ml of PBS(−) was poured into the flask and the flask was agitated thoroughly with its cap closed. After that, the cap was opened and the solution was discarded. Next, 10 ml of PBS(−) was poured into the flask in a clean bench, then the flask was thoroughly agitated with the cap closed, the cap was then opened and the solution was discarded.

The liquid remaining inside the flask and on the cap was aspirated thoroughly by suction, 10 ml of culture medium [44 ml of medium (RPMI1640+7), 1 ml of IL (interleukin)-2 at the concentration of 35,000 U/ml and 5 ml of human serum are mixed to be a culture medium (hereinafter, abbreviated to "culture medium")] was poured into the flask, stirred lightly, and cell suspension was transferred to the Flask. Ten μL of cell suspension was sampled for counting a number of cells and 1500 μL of the cell suspension was sampled for measuring contents of CD4 and CD8 positive cells (500 μl is sampled to each of three 1.5 ml tubes). The cultivation of the rest was started in a $CO_2$ incubator at 37° C. (Cultivation 0 day).

(3) <Counting a Number of Cells by Turk'S Solution>

In the above item. (2), 10 μL of collected umbilical cord blood was mixed with 40 μL of Turk's solution, the resulting solution of 10 μl was applied to a hemocytometer to count a number of cells under a microscope. As a result, a number of all cells in the flasks were $1.3 \times 10^6$, respectively.

(4) <Analysis of Cell Surface Antigen>

Three tubes of the suspension prepared in the above item (2) were centrifuged at 6,000 rpm at 4° C. for 5 minutes to precipitate the cells. After aspirating the supernatant clearly, 8 μL of PBS(−) and 8 μL of CD3/HLA-DR antibody were added to the tube No. 1, and 8 μL of PBS(−) and 8 μL of CD4/CD8 antibody were added to the tube No. 2, so that they were reacted for 30 minutes.

Besides, only 84 μL of PBS(−) was added to the tube No. 3 as a control for nonspecific reaction. After the incubation, 800 μL of sheath solution (Produced by Coulter Co. Ltd.; Isoton II) was added to every tube. After mixing with voltex mixer, centrifugation at 6,000 rpm at 4° C. for 5 minutes was performed to precipitate the cells. After aspirating the supernatant of every tube clearly, 800 μL of sheath solution was added to it. And then cell pellets were loosening by pipetting and transferred into a tube for FACS measurement.

In FACS analysis, FACScan (BD Bioscences, NJ USA) was used and measurement of FACS analysis was performed according to its manual. Contents of CD3+, HLA-DR+, CD4+ and CD8+ cells resulted 28%, 3%, 46% and 5%, respectively.

(5) <Preparation and Cultivation of the CD4+ Cell by Anti-CD8 Antibody Conjugated Magnetic Beads>

As a result of having cultivated in the above item (2), 5 days later, the total number of the cells became $3.4 \times 10^7$ and each number of CD4+ and CD8+ cells became $9.5 \times 10^6$. These cultured cells were transferred into a 50 ml tube, and centrifugation at 1,000 rpm at 20° C. for 10 minutes was performed. After the centrifugation, the supernatant was discarded and the cell precipitates were loosened well by vortex mixer.

On the other hand, 300 μL of the magnetic beads conjugated with anti-CD8 antibody containing 4 times beads as many as the number of CD8+ cells was put into a 15 ml tube and installed to a magnet MPC-1 to incubate for one minute. The resulting solution was taken out so as not to aspirate the beads and the tube was removed from the magnet. One ml of PBS(−) was added to the tube and stirred well, and then the tube was installed to the magnet. After the incubation for one minute, the resulting solution was taken out so as not to aspirate the beads and the tube was removed from the magnet. One ml of PBS(−) was put into the tube again and stirred well, and then the tube was installed to the magnet. After the incubation for one minute, the resulting solution was taken out so as not to suck up the beads and the tube was removed from the magnet.

Five ml of medium for reaction (prepared by mixing 45 ml of washing solution and 5 ml of human serum) was added to cell suspension collected by centrifuging and suspended lightly, then the cells were transferred into the tube including the magnetic beads conjugated with anti-CD8 antibodies, and the mixture if cells and beads were incubated in a cold room for 30 minutes as shaking lightly with a belly dancer laboratory shaker. After the incubation, the tube was installed to the magnet and incubated for one minute. The resulting solution was taken out so as not to aspirate the beads and transferred to a new 15 ml tube. One ml of PBS(−) was added to the former tube which contained the magnetic beads, the tube was installed to the magnet again and incubate for one minute. The 2nd resulting solution was taken out so as not to aspirate the beads, transferred into a new tube and centrifuged at 1,000 rpm at 20° C. for 10 minutes. After the centrifugation, the supernatant was discarded and the cell precipitates were loosened well by vortex mixer.

Ten ml of culture medium was added to the recovered CD4+ cells and the resulting matter was suspended lightly. On the other hand, solution of OKT3 in the OKT3 solidified flask (middle) produced similarly to the above item (1) was aspirated by suction. Ten ml of PBS(−) was poured into the flask, then the flask was thoroughly agitated with a cap of the flask closed, the cap was then opened and the solution was discarded. Next, 10 ml of PBS(−) was poured into the flask in a clean bench, then the flask was thoroughly agitated with the cap closed, the cap was then opened and the solution was discarded. The liquid remaining inside the flask and on the cap was aspirated thoroughly by suction and the cell suspension was transferred into the flask. Ten μL of suspension was sampled for counting a number of cells and 1,000 L of suspension was sampled for measuring content of CD4+ and CD8+ cells (500 μl is sampled to each of two 1.5 ml tubes). The cultivation of the rest was started in a $CO_2$ incubator at 37° C. (Cultivation 0 day)

(6) <Expanding Cultivation Of CD4+ Cell>

20 ml of culture medium was added to the cultivation medium in the above item (5) on the third day and the fourth day, respectively. Five days later, to expand the culture volume more, culture flask were changed from the flask (middle) to the flask (large) that was produced similarly to the above mentioned. Namely, the OKT3 solution in the OKT3 solidified flask (large) prepared in the same way as the above item (1) was aspirated by suction. 50 ml of PBS(−) was poured into the flask and the flask was agitated thoroughly with its cap closed. After that, the cap was opened and the solution was discarded.

Next, 50 ml of PBS(−) was poured into the flask in a clean bench, then the flask was thoroughly agitated with the cap closed, the cap was then opened and the solution was discarded.

Next, 50 ml of PBS(−) of 50 ml was poured into the flask aseptically, then the flask was thoroughly agitated with a cap of the flask closed, the cap was then opened and the solution was discarded. The liquid remaining inside the flask and on the lid was aspirated thoroughly by suction. The cells adhere to a bottom of the flask (middle) was detached from the bottom by tapping the flask several times and the cell suspension in the flask (middle) was transferred to the flask (large). Furthermore, 50 ml of flesh culture medium was put into the flask (middle) in order to suspend the remaining cells, and the cell suspension in the flask (middle) was transferred to a new flask (large) and the flask was incubated in the $CO_2$ incubator at 37° C. to continue the culture.

(7) <Cryopreservation of CD4+ Cell>

Regarding to cell culture in the above item (6), the cells were cryopreserved by a following method on the sixth day of the cultivation. In a method for preservation, the cells adhered to the bottom of the flask were detached by tapping the flask several times, then 500 μl of the culture medium in the flask was taken out and spread onto a tryptic soy agar (TSA) plate, and then the plate was incubated in the $CO_2$ incubator at 37° C. to carry out sterility testing. Furthermore, 10 μl of the culture medium in the flask was taken out and the number of cells was counted.

Next, 40 ml of the cultured cell solution was transferred to each of two 50 ml tubes, and they were centrifuged at 1,000 rpm at 20° C. for 5 minutes. In every tube, the supernatant was discarded and the cell pellet was vortexed, the resulting cell suspension and cell preservation solution [prepared by mixing 5 ml of human serum, 5 ml of dimethyl sulfoxide (hereinafter, abbreviated to DMSO) and a 40 ml of medium (RPMI1640+7)] were cooled down on an ice for 5 minutes, the cell suspension of every tube was brought together to one tube with 4.5 ml of the cell preservation solution, the cells in the tube were homogenized by pipetting lightly, and then the resulting matter was divided into three cryopreservation tubes (2.0 ml) respectively.

Furthermore, the tubes were put in a BICELL (Nihon Freezer co. Ltd., Tokyo Japan), a freezing container, and preserved at −80° C. for several days, and then preserved in a liquid nitrogen tank. The cell concentration at the culture was $1.9\times10^6$/ml, and the preserved cell number was $5.1\times10^7$/-tube.

(8) <Counting of a Number of Cells by Trypan Blue Dye Exclusion>

10 μl of the cell suspension sampled for counting cell number in the above item (7) was mixed with 20 μl trypan blue solution, the resulting matter was applied to hemocytometer to count the cell number under the microscope. Consequently, the total number of the cells was $5.1\times10^7$.

(9) <Course Before Cord Blood Transplantation and Administering Lymphocytes>

A patient with acute myelomonocytic leukemia could not be introduced to remission was carried out bone marrow transplantation from HLA-identical siblings, but 2 months later the leukemia relapsed. Then peripheral blood stem cell transplantation from same donor was carried out twice, blast cells still remained and the patient developed hematopoietic hypoplasia. GVHD was not observed in every 3 times transplantation. The same patient received umbilical cord blood transplantation with 3 loci mismatch and GVHD grade III was observed 10 days later. The severity of GVHD improved by mPLS pulse treatment. The three times of stem cell transplantations ended in failure. Since no GVHD developed and thus a GVL effect was not induced, it was determined that an activated CD4+ cell therapy was carried out because of expecting an anti-tumor effect after the transplantation and promoting of the donor cells survival.

(10) <Taking Out and Revival of Preserved CD4 Positive Cells>

One of the tube containing CD4+ cells cryopreserved in the above item (7) was taken out and then warmed up by a heat block at 37° C. for 4 minutes. Ten ml of washing medium (RPMI1640+6) was poured into a 15 ml centrifugation tube aseptically and then the preserved lymphocyte were suspended the medium with a transfer pipette. Furthermore, after centrifugation at 1,000 rpm at 20° C. for 5 minutes, the supernatant of it was discarded and tapped lightly, then the cell pellet was suspended to 50 ml of culture medium, and then the resulting cell suspension was transferred to a cloning plate.

After observing the cells by the microscope, the plate was incubated in the $CO_2$ incubator at 37° C. and the cultivation started again (Cultivation 0 day). On the second day of the cultivation, the vigorous growth of the cells all over the plate were confirmed under the microscope and then the cells in the cloning plate were transferred to a flask (225 cm$^2$, CELL CULTUREFLASK). Furthermore, after washing the cloning plate with 50 ml of fresh culture medium to recover the remaining cells, the cells were transferred to a flask and incubated in the $CO_2$ incubator at 37° C. to continue the cultivation.

On the fourth day of the cultivation, the OKT3 solution in the OKT3 solidified flask (large) produced similarly to the above item (5) was aspirated by suction. Fifty ml of PBS(−) was poured into the flask, then the flask was thoroughly agitated with a cap of the flask closed, the cap was then opened and the solution was discarded. Next, fifty ml of the PBS(−)=was poured into the flask aseptically, then the flask was thoroughly agitated with a cap of the flask closed, the cap was then opened and the solution was discarded by decanting.

The liquid remaining inside the flask and on the cap was aspirated thoroughly by suction. The cells adhered to the bottom of the used flask (middle) were detached by tapping the flask several times, and the cell suspension was transferred to the new flask (large). Furthermore, 150 ml of fresh culture medium was added to the used flask (middle) to suspend the remaining cells, and then the resulting suspension was transferred to the new flask (large). The new flask (large) was put in the $CO_2$ incubator at 37° C. for cultivation to continue the cultivation.

(11) <Cultivation of CD4 Positive Cells in a Bag for Cultivation>

On the sixth day of the cultivation, the cells adhered to the bottom of the flask used in the cultivation in the above item (10) were detached by tapping the flask several times, 1 ml of the culture medium in the flask was taken out and was spread onto a sabouraud dextrose agar plate (containing chloramphenicol) or a sheep blood agar plate equally, and the plates were incubated in the $CO_2$ incubator at 37° C. to carry out an sterility testing.

Ten μl of the culture medium in the flask was taken out to count the cell number similarly to the above item (7). A culture bag A-1000 (a bag for cell cultivation) containing 750 ml of medium in which is 1:1 mixture of AIM-V medium prepared for bag cultivation [which is that IL-2, human serum and oxaloacetic acid are added to the medium of 10 L so that the final concentrations of them become 200 U/ml, 1% and 1 mM, respectively] and CP-2 (LL-7.1) medium (1 L) was warmed up at 37° C.

The bag and a 50 ml syringe were connected each other aseptically and the whole of the culture medium in the flask was poured into the bag with the syringe. A tube from the bag was clamped by forceps, an end of the tube was sealed, and the bag was put in the $CO_2$ incubator at 37° C. for cultivation to continue the cultivation.

(12) <Sterility Testing and Endotoxin Assay of CD4 Cell>

On the seventh day of the cultivation (the day before administration), about 1 ml of the culture medium was sampled from a sampling port of the culture bag cultivated in the above item (7) by a 1 ml syringe with 24G injection needle aseptically. The solution sampled firstly was discarded, about 1 ml of the solution was sampled by the same syringe again, about 200 μl of the solution was spread onto the sheep blood agar plate and the rest of the solution was transferred into a dry heat sterilized conical test tube.

After cleaning the sampling port of the bag after sampling by the forceps clamping an alcohol cotton, the bag was put in the $CO_2$ incubator at 37° C. for cultivation to continue the cultivation. The agar plate was put in the $CO_2$ incubator at 37° C. for cultivation to carry out sterility testing, and the dry heat sterilized conical test tube was centrifuged at 1,500 rpm at 20 for 5 minutes.

One hundred μl of prepared main solution (A kit for endotoxin testing using a toxicolor system1S-200 set and a toxicolor system ET-1 set, Seikagaku Corp., Tokyo Japan) was put into three dry heat sterilized test tubes with a disposable micro pipette, respectively. One hundred μl of water for injection is put into the test tube for negative control and 100 μl of standard solution was put into the test tube for positive control with dry heat sterilized disposable capillary tip installed micro pipette. Furthermore, 80 μl of water for injection and 20 μl of the centrifuged culture supernatant were put into the test tube for sample with dry heat sterilized disposable capillary tip installed micro pipette. The three tubes were incubated in a water bath incubator at 37° C. for 30 minutes.

Thirty minutes later, 400 μl of 0.8 M acetic acid solution was added to each of three test tubes, the test tubes were stirred with vortex, and then 400 μl of the reaction solution of each test tube was transferred to 96 wells plate to measure values in absorbance at 405 nm (reference 630 nm) with a microplate reader. It was confirmed that five times as much as the value of the absorbance of the sample did not exceed to a value of the positive control.

(13) <FACS Analysis of CD4+ Cell for Administration Before Harvest>

Before harvesting the CD4+ cells, a part of the culture medium cultivated in the bag was taken out as sampl, the cell number was measured by a method similar to the above item (8) and the content of CD8+ cell was measured by a method similar to the item (4). Consequently, the total cell number was $3.0 \times 10^9$ including 0.8% of the CD8 cells. Due to the total cell number and the ratio that the FACS analysis CD8+ cell content by percentage, there were $1.5 \times 10^6$ CD8 cells.

(14) <Harvesting of CD4 Positive Cells>

Thousand ml of the culture medium cultivated in the bag in the above item (11) was transferred in a 250 ml centrifugation tube aseptically, and the tube was centrifuged at 1,500 rpm at 20° C. for 8 minutes. After the centrifugation, the supernatant of it was discarded, the cell pellet was loosened with vortex mixer, 200 ml of the cell washing solution was put into the centrifugation tube, and then it was centrifuged at 1,800 rpm at 20° C. for 8 minutes. After the centrifugation, the supernatant of it was discarded and the cell Pellet was loosened with vortex mixer. One hundred ml of the cell washing solution was put into the centrifugation tube, each of the cell suspension was transferred into two 250 ml. tubes, and then they were centrifuged at 1,800 rpm at 20° C. for 8 minutes. After the centrifugation, the supernatant of it was discarded, the cell pellet was loosened vortex mixer, and then 100 ml of the cell washing solution was put into the two 250 ml tubes, respectively.

After the centrifugation, the supernatant was discarded and the cell pellet was loosened vortex mixer well. And then the cells were suspended in a final solution (a solution for administering lymphocytes was made by putting 100 ml of saline and 5 ml of 20% human serum albumin solution into a 250 ml centrifugation tube to be a final solution) sufficiently, it was passed through a filter with 100 micro-mesh and then fluid volume of the cell suspension was measured. Besides, the cell suspension was sampled in order to count the cell number and the content of CD4.

50 ml syringe was connected with a separation bag (300 ml) to pour the cell suspension from the syringe to the separation bag. When the pouring was completed, liquid remained in the syringe was pushed out by an inner cylinder, and finally the tube was clamped by the forceps. The tube was sealed by a tube sealer and syringe was cut off by scissors. As a result of the measurement, the liquid volume was 100 ml and the total cell number was $2.5 \times 10^9$.

(15) <FACS Analysis of CD4+ Cell for Administration After Harvest>

FACS analysis of CD4+ cell for administration after harvest was performed by a method similar to the above item (4). Consequently, the content by percentage of CD4+ cell was 99.75% and that of CD8+ cell was 0.25%.

(16) <Administering CD4 Positive Cells to a Patient>

CD4+ cells prepared in the above item (14) were administered intravenously to the patient at ratio of $4.5 \times 10^7$/Kg body weight over one hour. Administration after that was carried out three times in every one or two weeks. One dose was $2.5 \times 10^6$ to $5.9 \times 10^7$/Kg body weight and was administered intravenously to the patient during one hour.

Embodiment No. 2

(1) <Collection of Blood from a Donor>

After the umbilical cord blood transplantation, the lymphocytes were infused nine times. Furthermore, to improve survival, 30 ml of peripheral blood was drawn from the vein of the patient with a syringe containing heparin on the 87th day after the transplantation.

(2) <Separation of Peripheral Blood Mononuclear Leukocytes>

A needle of an injection syringe collecting blood aseptically in a clean bench (hereinafter, abbreviated to "aseptically") was removed so as not to touch an adjacent to a connected portion of syringe and changed to 19G needle. Fifteen ml of the washing medium was poured into two 50 ml centrifugation tubes, respectively and the whole of the collected blood was poured into them equally slowly. After closing a cap of every centrifugation tube tightly, the diluted blood was mixed by turning the tube upside down twice or three times. Three ml of Lymphosepar I (IBL Co. Ltd., Gunma Japan), Ficoll-Conray solution, was put into six ml centrifugation tubes with a 10 ml pipette, respectively. Ten ml of diluted blood with the medium was layered carefully onto Lymphpsepar I in the every sedimentation tube undisturbed at the interface so, and then centrifuged at 1,800 rpm at 20° C. in the condition of braking off for 15 minutes.

After the centrifugation, the upper layer was drawn off by the aspirator aseptically to about 1 cm upper a lymphocyte layer so as not to aspirate the lymphocyte. The lymphocyte layer was taken out with a 5 ml pipette so as not to suck up a clot layer and transferred in a 50 ml centrifugation tube in which 25 ml of the washing medium (RPM11640+6) was put in advance. After a cap of the sedimentation tube was closed and mixed by turning the tube upside down twice or three times, the resulting matter was centrifuged at 1,800 rpm at 20° C. for 10 minutes. After the centrifugation, the supernatant was discarded and the cell pellet was loosened well with vortex mixer. Furthermore, after 50 ml of the washing medium was put into it and mixed by turning the tube upside down, 10 µl of the solution was sampled for counting cell number, 500 µl of the solution was sampled to two 1.5 ml micro tubes for measuring contents of CD4 and CD8, respectively.

(3) <Measurement of Cell Number by Turk'S Solution>

Ten µl of the cell suspension sampled for counting the cell number in the above item (2) was mixed with 40 µL of Turk's solution, 10 µl of the resulting matter was applied to a hemocytometer and the cell number was counted under a microscope, consequently the total of the cell number was $8.5 \times 10^7$.

(4) <Analysis of CD4 Positive Cells>

Two tubes containing the cell suspension prepared in the above item (2) was centrifuged at 6,000 rpm at 4° C. for 5 minutes to precipitate the cell and then the supernatant was aspirated clearly. Then, 8 µl of Dulbecco's phosphate-buffered saline and 8 µl of CD4/CD8 antibodies were put into two tubes, respectively and stirred well, and then were reacted at 4° C. for 30 minutes. After the reaction, 800 µl of the sheath solution was put into every tube and stirred by vortexing, and the resulting matter was centrifuged at 6,000 rpm at 4° C. for 5 minutes to precipitate the cells.

After aspirating the supernatant clearly, 800 µl of the sheath solution was added, the cells were loosened by pipetting, and then the resulting matter was put into a tube for FACS measurement. Besides, in FACS, FACScan was used. Measurement of FACS was performed according to the manual. Consequently, percentage of CD4+ or CD8+ cells was 28%, respectively. From the total cell number anf result of FACS analysis, the cell number of CD4+ or CD8+ cells was $2.4 \times 10^7$, respectively.

(5) <Preparation in OKT3 Solid Phased Flasks (Middle) and (Large)>

Five ml of OKT3 solution (5 µg/ml in PBS(−)) was put into a culture flask (middle) and 10 ml of the OKT3 solution was put into a culture flask (large), the solutions immersed bottoms of the flasks respectively, and they were preserved in a cold room just before use.

(6) <Separation and Cultivation of CD4+ Cells with Magnetic Bead Conjugated with Anti-CD8 Antibodies>

From 50 ml cell suspension prepared in the above item (2), 20 ml of cell suspension (the total cell number was $3.4 \times 10^7$ and the CD4 and CD8 positive cell number was $9.5 \times 10^6$ respectively) was transferred into a 50 ml tube, and centrifuged at 1,000 rpm at 20° C. for 10 minutes. After the centrifugation, the supernatant was discarded and the cell pellet was loosened well with vortex mixer.

Three hundred µL of magnetic bead conjugated with anti-CD8 antibody solution containing beads 4 times as many as the CD8+ cell number was put into the 15 ml tube, the tube was installed to a magnet MPC-1 to be reacted for one minute. Furthermore, the solution was taken out so as not to aspirate the beads, the tube was removed from the magnet, then 1 ml of the PBS(−) solution was put into the tube and stirred well, and then the tube was installed to the magnet again. After one minute reaction, the solution was taken out so as not to aspirate the bead, and then the tube was removed from the magnet. After 1 ml of the PBS(−) solution was put into the tube and stirred well again, and the tube was installed to the magnet.

After one minute reaction, the solution was taken out so as not to aspirate the beads and the tube was removed from the magnet.

Five ml of medium for reaction (prepared by mixing 45 ml of washing solution and 5 ml of human serum) was added to cell suspension collected by centrifuging and suspended lightly, then the cells were transferred into the tube including the magnetic beads conjugated with anti-CD8 antibodies, and the mixture of cells and beads were incubated in a cold room for 30 minutes as shaking lightly with a belly dancer laboratory shaker. After the incubation, the tube was installed to the magnet and incubated for one minute. The resulting solution was taken out so as not to aspirate the beads and transferred to a new 15 ml tube. The tube was installed to the magnet again, and incubated for one minute. The resulting solution was taken out so as not to aspirate the beads, the cells was transferred into a new tube and centrifuged at 1,000 rpm at 20° C. for 10 minutes. After the centrifugation, the supernatant was discarded and the cell precipitates were loosened well by vortex mixer.

Twenty ml of culture medium [44 ml of medium (RPMI1640+7), 1 ml of IL (interleukin)-2 at the concentration of 35,000 U/ml and 5 ml of human serum are mixed to be a culture medium (hereinafter, abbreviated to "culture medium")] was added to the recovered CD4+ cells and the resulting matter was suspended lightly. On the other hand, solution of OKT3 in the OKT3 solidified flask (middle) produced similarly to the above item (5) was aspirated by suction. Ten ml of PBS(−) was poured into the flask, then the flask was thoroughly agitated with a cap of the flask closed, the cap was then opened and the solution was discarded. Next, 10 ml of PBS(−) was poured into the flask in a clean bench, then the flask was thoroughly agitated with the cap closed, the cap was then opened and the solution was discarded.

The liquid remaining inside the flask and on the cap was aspirated thoroughly by suction and the cell suspension was transferred into the flask. Ten µL of suspension was sampled for counting a number of cells and 1,000 µL of suspension was sampled for measuring content of CD4+ and CD8+ cells (500 µl is sampled to each of two 1.5 ml tubes). The cultivation of the rest was started in a $CO_2$ incubator (95% humidity) at 37° C. (Cultivation 0 day). As a result from the analysis of CD4+ cells similarly to the above item (4), the content of the CD4+ cell was 46% and the content of CD8+ cell was 5%.

(7) <Counting of Cell Number by Trypan Blue Dye Exclusion>

Ten µl of the cell suspension sampled for counting cell number in the above item (6) was mixed with 20 µl of trypan blue solution, 10 µl of the resulting matter was applied to the hemocytometer under a microscope. As the result from cell counting, the total cell number was $2.6 \times 10^7$.

(8) <Expanding Culture of CD4+ Cell>

Twenty five ml of culture medium was added to the cultivation medium in the above item (6) on the third day and the fourth day, respectively. Five days later, to expand the culture volume more, culture flask were changed from the flask (middle) to the flask (large) that was produced similarly to the above mentioned. Namely, the OKT3 solution in the OKT3 solidified flask (large) prepared in the same way as the above item (5) was aspirated by suction. Fifty ml of PBS(−) was poured into the flask and the flask was agitated thoroughly with its cap closed. After that, the cap was opened and the solution was discarded.

Next, 50 ml of PBS(−) was poured into the flask in a clean bench, then the flask was thoroughly agitated with the cap closed, then the cap was opened and the solution was discarded. The liquid remained in the flask and on the lid was aspirated by suction thoroughly. The cells adhered to a bottom of the flask used in the cultivation so far were detached by tapping the flask several times lightly and then the cell suspension was transferred. Furthermore, 50 ml of new culture medium was put into the used flask to suspend the remained cells, and it was transferred to a new flask. The new flask was put in the $CO_2$ incubator at 37° C. to continue the cultivation.

(9) <Cryopreservation of CD4+ Cells>

A part of the cells cultivated in the above item (8) were cryopreserved once on the sixth day of the cultivation. In a method for preservation, the cells adhere to the bottom of the flask were detached by tapping the flask several times, then 500 µl of the culture medium in the flask was taken out and spread onto a tryptic soy agar (TSA) medium, and then incubated in the $CO_2$ incubator at 37° C. to carry out an sterility testing. Furthermore, 10 µl of the culture medium in the flask was taken out and the cell number was counted similarly to the above item (3).

Next, 40 ml of the cultured cell solution was transferred to each of two 50 ml tubes, and they were centrifuged at 1,000 rpm at 20° C. for 5 minutes. In every tube, the supernatant was discarded and the cell pellet was vortexed, the resulting cell suspension and cell preservation solution [prepared by mixing 5 ml of human serum, 5 ml of dimethyl sulfoxide (hereinafter, abbreviated to DMSO) and a 40 ml of medium (RPMI1640+7)] were cooled down on ice for 5 minutes, the cell suspension of every tube was brought together to one tube with 4.5 ml of the cell preservation solution, the cells in the tube were homogenized by pipetting lightly, and then the resulting matter was divided into three cryopreservation tubes (2.0 ml), respectively. Furthermore, the tubes were put in a BICELL (Nihon Freezer co. Ltd., Tokyo Japan), a freezing container, and preserved at −80° C. for several days, and then preserved in a liquid nitrogen tank. The cell concentration at the culture was $1.9 \times 10^6$/ml, and the preserved cell number was $5.1 \times 10^7$/tube.

(10) <Taking Out and Revival of Preserved CD4 Positive Cells>

One of the tube containing CD4+ cells cryopreserved in the above item (9) was taken out and then warmed up by a heat block at 37° C. for 4 minutes. Ten ml of washing medium (RPMI1640+6) was poured into a 15 ml centrifugation tube aseptically and then the preserved lymphocyte were put into the medium with a transfer pipette. Furthermore, after centrifugation at 1,000 rpm at 20° C. for 5 minutes, the supernatant of it was discarded and tapped lightly, then the cell pellet was suspended to 50 ml of culture medium, and then the resulting cell suspension was transferred to a cloning plate.

After observing the cells by a microscope, the plate was incubated in the $CO_2$ incubator at 37° C. and the cultivation started again (Cultivation 0 day). On the second day of the cultivation, the vigorous growths of the cells all over the plate were confirmed under the microscope and then the cells in the cloning plate were transferred to a flask (225 $cm^2$, CELL CULTUREFLASK). Furthermore, after washing the cloning plate with 50 ml of fresh culture medium to recover the remaining cells, the cells were transferred to a flask and incubated in the $CO_2$ incubator at 37° C. to continue the cultivation.

On the fourth day of the cultivation, the OKT3 solution in the OKT3 solidified flask (large) produced similarly to the above item (5) was aspirated by suction. Fifty ml of PBS(−) was poured into the flask, then the flask was thoroughly agitated with a cap of the flask closed, the cap was then opened and the solution was discarded. Next, fifty ml of PBS(−) was poured into the flask aseptically, then the flask was thoroughly agitated with a cap of the flask closed, the cap was then opened and the solution was discarded by decanting. The liquid remaining inside the flask and on the cap was aspirated thoroughly by suction.

The cells adhere to the bottom of the used flask (middle) were detached by tapping the flask several times, and the cell suspension was transferred to the new flask (large). Furthermore, 150 ml of fresh culture medium was added to the used flask (middle) to suspend the remaining cells, and then the resulting suspension was transferred to a new flask (large). The new flask (large) was incubated put in the $CO_2$ incubator at 37° C. to continue the cultivation.

(11) <Cultivation of CD4 Positive Cells in a Bag for Cultivation>

On the sixth day of the cultivation, the cells adhered to the bottom of the flask used in the cultivation in the above item (10) were detached by tapping the flask several times, 1 ml of the culture medium in the flask was taken out and was spread onto a sabouraud dextrose (with chloramphenicol) agar plate and a sheep blood agar plate equally, and the plates were incubated in the $CO_2$ incubator at 37° C. to carry out an sterility testing.

Ten of the culture medium in the flask was taken out to count the cell number similarly to the above item (7). A culture bag A-1000 (a bag for cell cultivation) containing 750 ml medium in which is 1:1 mixture of AIM-V medium prepared for bag cultivation [which is that IL-2, human serum and oxaloacetic acid are added to the medium of 10 L so that the final concentrations of them become 200 U/ml, 1% and 1 mM, respectively] and CP-2 (LL-7.1) medium (1 L) was warmed up at 37° C. The bag and a 50 ml syringe were connected each other aseptically and the whole of the culture medium in the flask was poured into the bag with the syringe. A tube from the bag was clamped by a forceps, an end of the tube was sealed, and the bag was put in the $CO_2$ incubator for cultivation at 37° C. to continue the cultivation.

(12) <Sterility Testing and Endotoxin Assay of CD4 Cell>

On the Seventh day of the cultivation (the day before administration), about 1 ml of the culture medium was sampled from a sampling port of the culture bag cultivated in the above item (7) by a 1 ml syringe with 24G injection needle aseptically. The first solution was discarded, about 1 ml of the solution was sampled by the same syringe again, about 200 µl of the solution was plated onto the sheep blood agar plate and the rest of the solution was put into a dry heat sterilized conical test tube.

After cleaning the sampling port of the bag after sampling with an alcohol cotton swab clamped by a forceps, the bag was put in the $CO_2$ incubator for cultivation at 37° C. to continue the cultivation. The agar plate was put in the $CO_2$ incubator at 37° C. for cultivation to carry out an sterility testing, and the dry heat sterilized conical test tube was centrifuged at 1,500 rpm at 20 for 5 minutes.

One hundred µl of prepared main solution was put into three dry heat sterilized test tubes with dry heat sterilized disposable capillary tip installed micro pipette, respectively. 100 µl of water for injection is put into the test tube as negative control and 100 µl of standard solution was put into the test tube as positive control with dry heat sterilized disposable capillary tip installed micro pipette, respectively. 80 µl of water for injection and 20 µl of the centrifuged culture supernatant were put into the test tube for sample with toxipett sampler. The three tubes were incubated in a water bath incubator at 37° C. for 30 minutes.

30 minutes later, 400 µl of 0.8 M acetic acid solution was added to each of three test tubes, the test tubes were stirred with vortex mixer, and then 400 µl of the reaction solution of each test tube was transferred to 96 wells plate to measure values in absorbance 405 nm (reference 630 nm) with a microplate reader. It was confirmed that five times as much as the value of the absorbance of the sample did not exceed to a value of the positive control.

(13) <FACS Analysis of CD4+ Cell for Administration Before Harvest Collection>

Before harvesting the CD4+ cells, a part of the culture medium cultivated in the bag was sampled, the cell number was measured by a method similar to the above item (7) and the content of CD8+ cell was measured by a method similar to the item (4). Consequently, the total cell number was $4.0 \times 10^9$ including 0.8% of the CD8 cells. Due to the total cell number and the ratio that the FACS analysis CD8+ cell count by percentage, there were $2.0 \times 10^6$ CD8+ cells.

(14) <Harvesting of CD4+ Cells>

1000 ml of the culture medium cultivated in the bag in the above item (12) was transferred in 250 ml centrifugation tubes aseptically, and the tubes were centrifuged at 1,500 rpm at 20° C. for 8 minutes. After the centrifugation, the supernatant was discarded, the cell pellet was loosened with vortex mixer, 250 ml of the cell washing solution was put into the centrifugation tube, and then it was centrifuged at 1,800 rpm at 20° C. for 8 minutes. After the centrifugation, the supernatant of it was discarded and the cell precipitate was loosened by vortexing. 100 ml of the cell washing solution was put into the sedimentation tube, each of the cell suspension was transferred into two 250 ml tubes, and then they were centrifuged at 1,800 rpm at 20° C. for 8 minutes. After the centrifugation, the supernatant was discarded, the cell precipitate was loosened by vortexing, and then 50 ml of the cell washing solution was put into the two 250 ml tubes respectively.

After the centrifugation, the supernatant was discarded and the cell pellet was loosened well with vortex mixer. The cells were suspended in a final solution (a solution for administering lymphocyte was made by putting 100 ml of saline and 5 ml of 20% human serum albumin solution into a 250 ml centrifugation tube to be a final solution) sufficiently, it was passed through a filter with 100 micro-mesh and then fluid volume of the cell suspension was measured.

Besides, the cell suspension was sampled in order to count the cell number and the content of CD4. 50 ml syringe was connected with a separation bag (300 ml) to pour the cell suspension through the syringe into the separation bag. When the pouring was completed, liquid remained in the syringe was pushed out by an inner cylinder, and finally the tube was clamped by a forceps. The tube was sealed and syringe was cut off by scissors. As a result of the measurement, the liquid volume was 100 ml and the total cell number was $3.7 \times 10^9$.

(15) <FACS Analysis of CD4+ Cell for Administration After Harvest>

FACS analysis of CD4+ cell for administration after harvest was performed by a method similar to the above item (4) of the embodiment No. 1. Consequently, the content by percentage of CD4+ cells was 99.75% and that of CD8+ cells was 0.25%.

(16) <Administering CD4+ Cells to a Patient>

CD4+ cells prepared in the above item (14) were administered intravenously to the patient at ratio of $3 \times 10^7$/Kg body weight over one hour. Administration after that was carried out three times a week. One dose was $3 \times 10^6$ to $9 \times 10^7$/Kg body weight and was administered intravenously to the patient during one hour.

Embodiment NO. 3

(1) <Measuring Immunogloblin Level in Blood>

As a result of measuring the level of immunogloblin in a patient's peripheral blood, the immunogloblin level was increased from the early stage of clinical course. Besides, relapse was recognized in a patient in two months after the transplantation. In this case, as the blast cells became the majority of blood cells, a number of lymphocytes was decreased, but the immunogloblin level remained within a normal range, so that immunoglobulin replacement therapy was not necessary.

In spite of decreasing neutrophils or lymphocytes remarkably, the patient did not suffered with serious infectious disease. Thus, it was found that ability of immune response of the patient was increased remarkably by administering the CD4+ cells. Besides, according to production of antibodies from early stage after transplantation in umbilical cord blood transplanted patient, it is clear that donor derived activated lymphocyte promoted survival of hematopoietic cells and promoted antibody production.

What is claimed is:

1. A method for promoting survival of hematopoietic stem cells that have been transplanted to a patient, comprising:
    a process for separating mononuclear cells including lymphocytes from umbilical cord blood;
    activating and proliferating the lymphocytes with anti-CD3 antibody and/or interleukin-2;
    selecting CD4 positive cells from the activated and proliferated lymphocytes;
    activating and proliferating the selected CD4 positive cells with anti-CD3 antibody and/or interleukin-2;
    cryopreserving the activated and proliferated CD4 positive cells for use in the patient being transplanted with hematopoietic stem cells from umbilical cord blood and in need of the activated and proliferated CD4 positive cells;
    preparing a formulation for administration from the cryopreserved CD4 positive cells; and
    administering the formulation to the patient who recently received transplantation with hematopoietic stem cells from umbilical cord blood.

2. The method of claim 1, wherein the lymphocytes are HLA-matched to the hematopoietic stem cells previously transplanted to the patient.

3. The method of claim 2, wherein the lymphocytes are HLA-matched to not less than three primary HLA loci selected from the group consisting of loci A, B, C, DR, DQ and DP.

* * * * *